United States Patent
Burwinkel et al.

(10) Patent No.: US 12,374,456 B2
(45) Date of Patent: Jul. 29, 2025

(54) TRAINING DOMAIN-BASED AI BOOSTING OF AN IOL DETERMINATION

(71) Applicant: Carl Zeiss Meditec AG, Jena (DE)

(72) Inventors: Hendrik Burwinkel, Oberkochen (DE); Michael Trost, Oberkochen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/476,261

(22) Filed: Sep. 27, 2023

(65) Prior Publication Data

US 2024/0112799 A1 Apr. 4, 2024

(30) Foreign Application Priority Data

Sep. 30, 2022 (DE) .......................... 102022125419.4

(51) Int. Cl.
| | |
|---|---|
| G16H 40/63 | (2018.01) |
| G06N 20/20 | (2019.01) |
| A61B 3/00 | (2006.01) |
| G01M 11/02 | (2006.01) |

(52) U.S. Cl.
CPC ............ *G16H 40/63* (2018.01); *G06N 20/20* (2019.01); *A61B 3/0025* (2013.01); *G01M 11/0228* (2013.01)

(58) Field of Classification Search
CPC ........ G16H 40/63; G16H 50/20; G06N 20/20; A61B 3/0025; G01M 11/0228; G02C 7/022
See application file for complete search history.

(56) References Cited

U.S. PATENT DOCUMENTS

2019/0099262 A1 * 4/2019 Ladas ................... A61F 2/1613

FOREIGN PATENT DOCUMENTS

| CN | 111565677 | * | 1/2019 | ............... A61F 2/16 |
| CN | 112599244 A | * | 4/2021 | |
| DE | 102020101762 A1 | | 7/2021 | |
| DE | 102020101763 A1 | | 7/2021 | |
| DE | 102021102142 A1 | | 8/2022 | |
| WO | WO-2010065475 A2 | * | 6/2010 | ........... A61B 3/0025 |
| WO | WO-2021148517 A1 | * | 7/2021 | ............... A61F 2/16 |

OTHER PUBLICATIONS

German Patent and Trademark Office. Response to Office Action relating to applicaiton No. 102022125419.4, dated May 31, 2023.

* cited by examiner

*Primary Examiner* — Maurice C Smith
(74) *Attorney, Agent, or Firm* — Honigman LLP; Brett A. Krueger

(57) ABSTRACT

A computer implemented method for determining a refractive power value of an intraocular lens to be inserted is described. The method includes measuring ophthalmological patient data, receiving a target refraction value, determining a first refractive power value of an intraocular lens to be inserted, with the measured ophthalmological patient data and the target refraction value being used as input data, determining, by means of a trained machine learning system, a second refractive power value of the intraocular lens to be inserted, the measured ophthalmological patient data and the received target refraction value being used as input data for the trained machine learning system, and determining the final refractive power value of the intraocular lens to be inserted from the first refractive power value and the second refractive power value by means of an individual boosting factor value.

11 Claims, 8 Drawing Sheets

TRAINING DOMAIN-BASED AI BOOSTING OF AN IOL DETERMINATION

CROSS REFERENCE TO RELATED APPLICATIONS

This U.S. patent application is a continuation of, and claims priority under 35 U.S.C. § 119(d) to German Patent Application DE 10 2022 125 419.4, filed on Sep. 30, 2022. The disclosure of this prior application is considered part of the disclosure of this application and is hereby incorporated by reference in its entirety.

TECHNICAL FIELD

This disclosure relates to a computer-implemented method for determining a refractive power value of an intraocular lens to be inserted. The disclosure also relates to a system for determining a refractive power value of an intraocular lens to be inserted, and to a corresponding computer program product.

BACKGROUND

These days, a multiplicity of different scientific fields are stimulated by the use of artificial intelligence (AI). AI and machine learning (ML) systems which use prediction models have developed into powerful tools. This also applies to a broad use in various medical fields. By now, a physician or assistant is able to use these tools largely without effort in order to obtain good predictions and recommendations for an upcoming medical task. In this case, the correct selection of parameters—or hyperparameters—for the underlying prediction model and also the amount and quality of training data are of decisive importance. Thus, the training data must cover, to the best possible extent, the area in which a prediction is intended to be made.

Outside of this coverage or this domain and the property of machine learning models, which often have a highly nonlinear character, said machine learning models are susceptible to unexpected prediction values which do not meet the needs of the actual task. In individual medical fields, there often is only a comparatively small amount of usable training data available for a domain. It is also possible that comparatively few usable training data are available for different domains—i.e., for uses with a different initial medical assumption.

Nevertheless, physicians would still like to be able to use the available machine learning models even for those areas which are not directly covered by the available training data. This also applies to the field of ophthalmology, for example within the scope of cataract operations in which the natural lens of the eye is replaced by an intraocular lens to be inserted. An important parameter for such operations is a recommendation or a prediction, by the trained machine learning system, of the refractive power for the intraocular lens intended to be inserted.

On account of the different types and different manufacturers of intraocular lenses, there frequently is available only a small amount of training data for individual types or lenses from different manufacturers, with the result that the prediction of the machine learning systems supplies reliable prediction values only within relatively tightly delimited ranges. On the one hand, physicians like to use these systems, trained thus, directly for the tightly delimited range, but also have the fundamental urge to use the trained models in ranges that are not directly covered, or covered poorly, by the training data.

Thus, there is a need to propose a method and a system which precisely fulfil the requirements described hereinabove, specifically the possibility of using a machine learning system for a prediction in the medical field, in particular in ophthalmology, which system supplies reliable prediction values—for example for the refractive power of an intraocular lens to be inserted—both within the domain of available training data and outside thereof.

SUMMARY

According to a first aspect of the present disclosure, a computer-implemented method for determining a refractive power value of an intraocular lens to be inserted is presented. In this context, the method includes measuring ophthalmological patient data and receiving a target refraction value.

Further, the method includes determining, by means of a physical model, a first refractive power value of an intraocular lens to be inserted, with the measured ophthalmological patient data and the target refraction value being used as input data, and determining, by means of a trained machine learning system, a second refractive power value of the intraocular lens to be inserted, which machine learning system was trained using ophthalmological training data, respectively associated target refraction values and respectively associated refractive power values of an intraocular lens to be inserted, the respectively associated refractive power values of an intraocular lens to be inserted serving as ground truth data for determining a corresponding machine learning model for the machine learning system, the measured ophthalmological patient data and the received target refraction value moreover being used as input data for the trained machine learning system.

Finally, the method includes determining the final refractive power value of the intraocular lens to be inserted from the first refractive power value and the second refractive power value by means of an individual boosting factor value, the boosting factor being indicative of how well a patient vector, whose components are determined by the measured ophthalmological input data, fits to a domain of the training data used to train the machine learning system.

According to a second aspect of the present disclosure, a computer-implemented method for determining a target refraction value on the basis of a refractive power of an intraocular lens to be inserted is presented. The method includes measuring ophthalmological patient data and receiving a refractive power value of the intraocular lens to be inserted.

The method further includes determining, by means of a physical model, a first target refraction value, with the measured ophthalmological patient data and the refractive power value of the intraocular lens to be inserted being used as input data, and determining, by means of a trained machine learning system, a second target refraction value. In this case, the machine learning system was trained using ophthalmological training data, respectively associated refractive power values of the intraocular lens to be inserted and respectively associated target refraction values—or refractive results for the patient's eye with the inserted intraocular lens. The respectively associated target refraction values—or the refractive results for the patient's eye with the inserted intraocular lens—serve as ground truth data for determining a corresponding machine learning model for the machine learning system.

The measured ophthalmological patient data and the received refractive power value can then be used as input data for the trained machine learning system.

Finally, the method also includes determining a final target refraction value from the first target refraction value and the second target refraction value by means of an individual boosting factor value, the boosting factor being indicative of how well a patient vector, whose components are determined by the measured ophthalmological input data, fits to a domain of the training data used to train the machine learning system.

According to a third aspect of the present disclosure, a system for determining a refractive power value of an intraocular lens to be inserted is presented, the system being able to be considered to be associated with the method of the first aspect. This system comprises a processor, a memory which operatively cooperates with the processor to store instructions which, when executed by the processor, prompt the processor to measure—in particular by means of a measuring unit—ophthalmological patient data and to receive—for example using a reception unit—a postoperative target refraction value which can be achieved by the inserted intraocular lens.

The processor may also be prompted to determine, by means of a physical model—in particular by means of a determination unit for a physical model—a first refractive power value, with the measured ophthalmological patient data and the target refraction value being used as input data.

The processor may moreover be prompted to determine, by means of a trained machine learning system, a second refractive power value, which machine learning system was trained using ophthalmological training data, respectively associated target refraction values and respectively associated refractive power values of the intraocular lens to be inserted, the respectively associated refractive power values serving as ground truth data for determining a corresponding machine learning model for the machine learning system.

In this case, the measured ophthalmological patient data and the received target refraction value can be used as input data for the trained machine learning system.

Finally, the processor may also be prompted to determine a final refractive power value—e.g., by means of a determination unit for the final refractive power value—from the first refractive power value and the second refractive power value by means of an individual boosting factor value, the boosting factor being indicative of how well a patient vector, whose components are determined by the measured ophthalmological input data, fits to a domain of the training data used to train the machine learning system.

According to a fourth aspect of the present disclosure, a system for determining a target refraction value on the basis of a refractive power of an intraocular lens to be inserted is presented, the system being able to be considered to be associated with the method of the second aspect. This system comprises a processor, a memory which operatively cooperates with the processor to store instructions which, when executed by the processor, prompt the processor to measure—in particular by means of a measuring unit— ophthalmological patient data and to receive—in particular by means of a reception unit—a refractive power value of the intraocular lens to be inserted.

The processor may further be prompted to determine, by means of a physical model, a first target refraction value, with the measured ophthalmological patient data and the refractive power value of the intraocular lens to be inserted being used as input data, and to determine, by means of a trained machine learning system, a second target refraction value, which machine learning system was trained using ophthalmological training data, respectively associated refractive power values of the intraocular lens to be inserted and respectively associated target refraction values, the respectively associated target refraction values serving as ground truth data for determining a corresponding machine learning model for the machine learning system, the measured ophthalmological patient data and the received refractive power value being used as input data for the trained machine learning system.

Finally, the processor may also be prompted to determine a final target refraction value—or else a resultant refraction value, in particular by way of a determination unit for final target refraction value—from the first target refraction value and the second target refraction value by means of an individual boosting factor value, the boosting factor being indicative of how well a patient vector, whose components are determined by the measured ophthalmological input data, fits to a domain of the training data used to train the machine learning system.

The proposed computer-implemented method for determining a refractive power value—or else for determining a resultant refraction value—of an intraocular lens to be inserted has a plurality of advantages and technical effects, which may also apply accordingly to the associated systems:

The above-described object is advantageously solved by the method and system proposed here by virtue of using both a conventional method for predicting the refractive power (or target refraction value) together with a machine learning system, with moreover a boosting factor value being determined, the latter expressing how well measured patient data fit to the domain of the training data for the machine learning system.

Expressed in simple terms, the prediction value of the machine learning system is apportioned less significance in the case of poor correspondence of the measured patient data with the original set of training data for the machine learning system for the prediction of the refractive power/the resultant refraction value of the intraocular lens to be inserted. The greater the correspondence of measured patient data— in particular the greater the correspondence of the measured ophthalmological data—with the domain of the training data, the more highly the prediction value of the machine learning system is rated and also taken into account.

In this way, a trained machine learning system can be used for a prediction of the refractive power (or the resultant refraction value) of an intraocular lens to be inserted, both in those ranges in which the ophthalmological patient data correspond well with the range of the training data, and also in other ranges in which the ophthalmological patient data correspond less well to the range of the training data. In such a case, a used conventional method for determining a refractive power of an intraocular lens to be inserted is rated more highly.

Hence, such a system can be used even in those cases in which the measured data from a patient do not fall directly in the training domain of the machine learning system. The described approach always allows a stable prediction to be performed since the conventional method gradually takes over as soon as little to no added value is to be expected from the machine learning system. For well-trained ranges, the machine learning system can still implement its advantages in full and without impairment. The used boosting factor thus allows an unimpeded performance with great stability of the prediction at the same time.

The proposed method or system thus overcomes the limitations which exist if only a small amount of training data is available for individual lens types, thus limiting the prediction accuracy of the machine learning system, especially if the measured ophthalmological patient data do not correspond with the range of the original training data set for the machine learning system.

In this way, the physician is protected from using different machine learning systems with potentially different user interfaces, each of which would mean a deviation from surgical routine. They can use the same machine learning system in each case, even though there is no ideal correspondence between ophthalmological patient data and an original training data set.

Moreover, use can be made here of different conventional methods which allow the determination of the refractive power of the intraocular lens using different approaches, for example physical models, regression models or rule-based decision support systems.

This integration of conventional methods and a machine learning system-based approach, in which only a small amount of training data is available for individual ranges, is significantly superior to previously used approaches on account of its implicit integration. By way of example, conventional approaches would see the use of the machine learning system be preceded by a "manual" decision as to whether the machine learning system can be used on account of having been trained using the "correct" training data, which is to say training data in which the measured ophthalmological patient data are also situated. Should this not be the case, there is a pivot to a different conventional method or a different machine learning system. However, this would be a procedure that is susceptible to errors, and it can be overcome by means of the proposed concept.

An alternative method could consist of adding artificially generated data points, which were generated by conventional determination models, to the training data set. However, this would weaken or reduce the prediction accuracy of the machine learning system in its core region, specifically in the range of measured patient-based training data.

Consequently, both previously used alternative methods are significantly inferior to the concept proposed here. The automatic fine tuning between determining the refractive power of the intraocular lens firstly on the basis of conventional methods and secondly on the basis of the trained machine learning system depending on measured patient data cannot be provided by the known procedures. Especially the gradual and automated transition of the use of the prediction values from the machine learning system for the refractive power of the intraocular lens to be inserted to the conventional method for determining the refractive power, brought about by use of the boosting factor value, cannot be provided by previously known methods and systems.

Moreover, there can also be a clear indication to the physician regarding the ratio with which the results of the machine learning system and a conventional approach have been weighted in order to make a prediction for a refractive power of the intraocular lens to be inserted. In this context, this value may vary in a range from 0% to 100%.

Moreover, the proposed concept can also be reversed in term of content. Should the surgeon in that case select a real existent intraocular lens, they can let the expected resultant refraction value be predicted and thus be assisted with the selection of the correct intraocular lens if the result of the prediction proposes a refractive power value that does not exist in reality for any specific lens (e.g., 20.555 dioptre).

Further exemplary embodiments are presented below, which can have validity both in conjunction with the method and in conjunction with the corresponding system.

According to an advantageous embodiment of the method for predicting a refractive power of an IOL (intraocular lens), the final refractive power value of the intraocular lens to be inserted can be determined from the first refractive power and the second refractive power by means of the individual boosting factor value, in accordance with the following:

$$PowerIOL=BF*\text{second refractive power value}+(1-BF)*\text{first refractive power value}.$$

In this context, PowerIOL=final refractive power value of the intraocular lens to be inserted, and BF=boosting factor value. In this way, it is possible to elegantly ensure that either the first refractive power from the physical model or the second refractive power from the machine learning system can be weighted more. By way of example, if the boosting factor value is small, the physical model would be used to a significantly greater extent in the calculation of the final refractive power than the result of the machine learning system, and vice versa. Since the boosting factor fundamentally is a measure of how well the measured patient data fit to the training data set—i.e., belong to the same domain—the weighting of both components of the formula above is automatically to the correct extent.

According to an additional embodiment of the method for predicting a refractive power of an IOL, a determination of the individual boosting factor value may include applying a statistical analysis method to the ophthalmological training data and, on the basis thereof, there can then be a determination of an average vector from the training data set—i.e., the mean value of each individual vector component—and a determination of a covariance matrix. This may then represent the basis for the comparison with the measured patient data.

According to a further detailed embodiment of the method for predicting a refractive power of an IOL, the determination of the individual boosting factor value may include using a multivariate Gaussian function which was determined using the ophthalmological training data which are representable as vectors—these are vectors that were determined. The use of the multivariate Gaussian function is one of the possible options lending themselves on account of the assumption that there is symmetry with regards to the mean value.

According to an extended embodiment of the method for predicting a refractive power of an IOL, the determination of the individual boosting factor value may also include scaling a distribution density value ($\in \mathbb{R}$) which arises as the result of using the multivariate Gaussian function to an interval of [0, 1]. This is helpful, inter alia, because the distribution density value typically is of the order of $10^{-2}$ ... $10^{-3}$, with a very rapid drop to $10^{-6}$, ... $10^{-8}$. For the aforementioned formula for calculating the final refractive power, however, a boosting factor value in the interval [0, 1] is not only very helpful but also represents an order of magnitude that is mathematically meaningful and manageable as well.

According to a further embodiment, the method for predicting refractive power of an IOL may include transmitting the final refractive power value and/or the individual boosting factor value to at least one output device—e.g., to a monitor, to a digital display, to a head-up display, into a surgical microscope display, etc. Hence, by way of the visual perception of the individual boosting factor value, the surgeon can develop a feeling with regards to how good the prediction quality of the system is. In addition, the results of the first and the second refractive power determination of the final refractive power determination and of the target refraction values can naturally also be displayed.

At this point, attention is additionally drawn to the fact that the two proposed methods—and equivalently also the two corresponding systems—are equivalent to one another. Either a target refraction value is used as an input datum, as a result of which there then is—together with the patient data—a final refractive power determination for an intraocular lens. Then again, the refractive power of an intraocular lens to be inserted can be used as input datum, from which the corresponding system then determines the target refraction value—in this case thus the actual refraction value (i.e., consequently the resultant refraction value) after the operation.

This may be a great help to the surgeon for at least one reason. For example: An ideal refractive power value of for example 20.256, which has no physical correspondence in the range of usable intraocular lenses, was determined for given ophthalmological patient data and a given target refraction value. In this case, the surgeon would thus probably have to make a decision between 20.25 and 20.26. Naturally, they would then also have the desire to know the final refraction value that would then arise for this specific lens type after the operation. Since a specific target refraction value (e.g., slightly myopic) is sought after during normal ophthalmological operations, the surgeon would apply the proposed method according to the second aspect.

For this reason, at least all dependent claims should be applied both to the method of the first aspect and to the method of the second aspect. A corresponding statement likewise applies to both the system according to the third aspect and the system according to the fourth aspect, which was proposed hereinabove. A precondition here is that different training data are used: Thus, the patient data, the target refraction value and finally the determined final IOL refractive power are used as ground truth data in the first case and the patient data, the planned final IOL refractive power and finally the resultant refraction value are used as ground truth data in the second case.

Thus, the formula for determining the final resultant refraction value would be as follows:

Resultant refraction value=$BF$*second refraction value+$(1-BF)$*first refraction value.

Furthermore, embodiments can relate to computer program products able to be accessed from a computer-usable or computer-readable medium that comprises program code for use by, or in conjunction with, a computer or other instruction processing systems. In the context of this description, a computer-usable or computer-readable medium can be any device that is suitable for storing, communicating, transferring, or transporting the program code.

DESCRIPTION OF DRAWINGS

It is pointed out that exemplary embodiments of the disclosure may be described with reference to different implementation categories. In particular, some exemplary embodiments are described with reference to a method, whereas other exemplary embodiments may be described in the context of corresponding devices. Regardless of this, it is possible for a person skilled in the art to identify and to combine possible combinations of the features of the method and also possible combinations of features with the corresponding system from the description above and below—if not specified otherwise—even if these belong to different claim categories.

Aspects already described above and additional aspects of the present disclosure will become apparent inter alia from the exemplary embodiments described and from the additional further specific configurations described with reference to the figures.

Like reference symbols in the various drawings indicate like elements.

DETAILED DESCRIPTION

Figure 1:
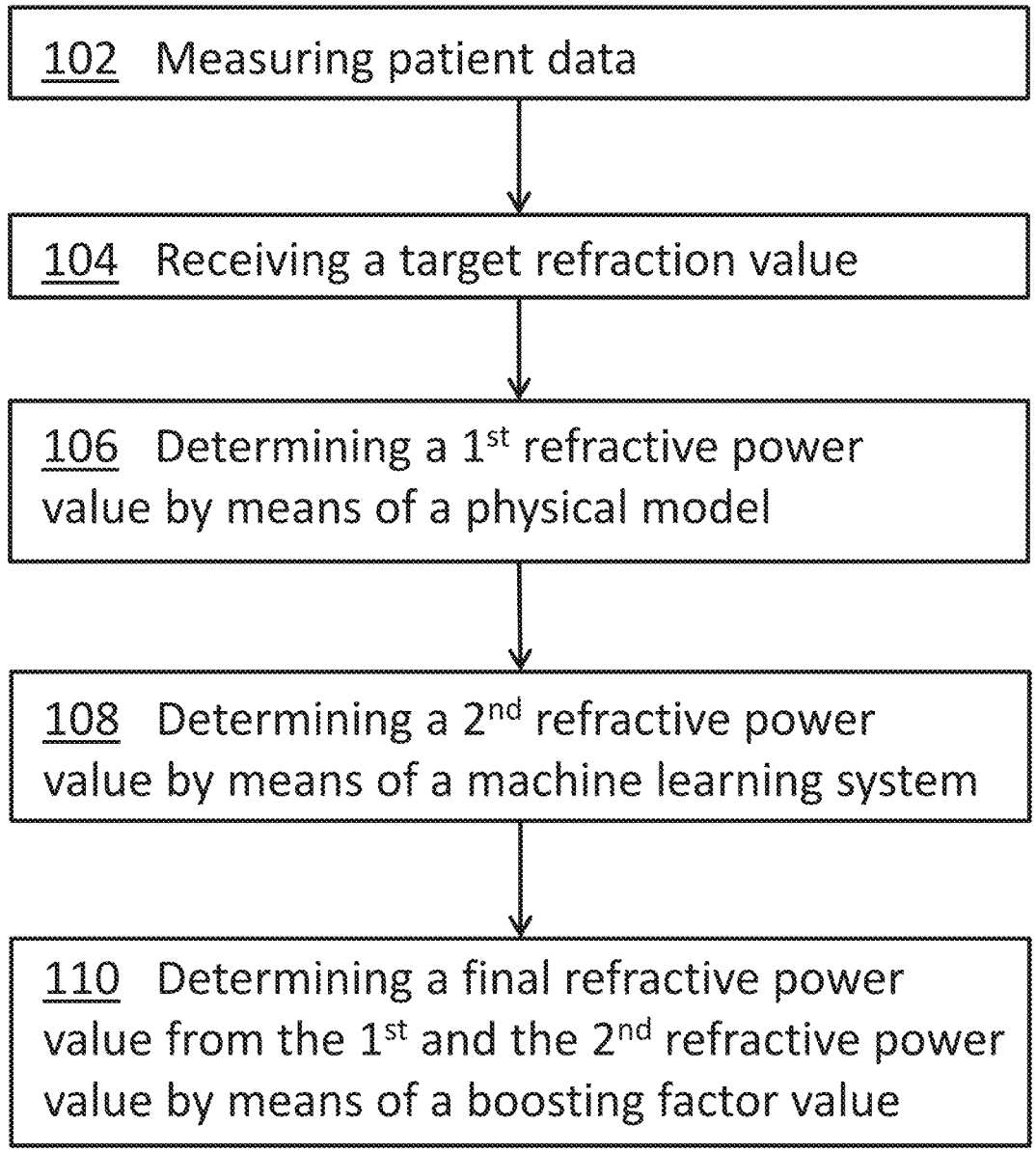
FIG. 1 illustrates a flowchart-like representation of an exemplary embodiment of the computer-implemented method according to the disclosure for determining a refractive power value of an intraocular lens to be inserted.

In the context of this description, conventions, terms and/or expressions should be understood as follows:

Here, the term "intraocular lens" (IOL) describes an artificial lens which is introduced into an eye, for example within the scope of a cataract operation, whereby the natural lens of the eye is replaced.

The term "ophthalmological patient data" or simply "patient data" may in this case describe patient-specific measurement data from a patient's eye, which are available preferably directly or in buffer-stored form—e.g., in a patient measurement data memory.

The term "target refraction value" may in this case describe the refraction value desired after surgery.

The term "resultant refraction value" may in this case describe the refraction value obtained after surgery by a specific IOL, which should actually be inserted, if, inter alia, the refractive power of the actually used IOL is used as input data.

The term "physical model" or "physical-optical model" may describe known dependencies of a refractive power of an IOL to be inserted on ophthalmological data, using a formula or relation. Various models are known.

The term "machine learning system" may describe a non-procedural system whose behavior in relation to input data and output data generated therefrom (or in relation to vectors in each case) is conditioned by a learning process in which example data—i.e., both input data and output data—are used. Parameter values of the learning system are optimized during the learning process (generally by minimizing a loss function), with the result that a machine learning model for predicting output data on the basis of unknown input data is available after the learning or training has been completed. By way of example, the optimization process can be implemented by way of a back-propagation function of differences between generated output data on desired output data. Various architectures for machine learning systems are known. Examples include a neural network and a deep neural network.

In general, the term "ground truth data" describes target data or desired prediction results of a prediction of the machine learning system which are used for the purpose of conditioning the machine learning system, which is to say for determining the parameter values, during the training of the machine learning system.

The term "machine learning model" usually describes a set of parameters which make up the machine learning model. The latter is used in the machine learning system. Optionally, additional configuration parameters of the machine learning system (i.e., hyperparameters) may also be contained in the learning model.

In this case, the term "final refractive power value" describes the actual refractive power of the IOL which is supplied by the proposed method as a result—consisting of a combination of a conventional and an ML-based approach.

The term "boosting factor" describes a value which is representable as a decimal number and which is indicative of how well a certain set of (measured) patient data fits to the training data used for training the machine learning system. In this case, "fits" is intended to mean that the patient data could by all means also lie within the set of training data. However, if the measured patient data are located outside of a boundary of the training data set, this would indicate that the patient data set does not fit directly to the training data. As a result, the determined refractive power value from the physical model would be weighted excessively—in accordance with the concept presented here.

In this case, the term "domain of the training data" describes in particular a set of training data which together have certain properties, for example are grouped around a mean value and in the process do not have a greater distance therefrom than a distance determined in advance. "Outlier data" should not be contained in the training data set.

A detailed description of the figures is given below. It is understood in this case that all of the details and information in the figures are illustrated schematically. A flowchart-like representation of an exemplary embodiment of the computer-implemented method according to the disclosure for determining a refractive power value of an intraocular lens to be inserted is depicted initially. Further exemplary embodiments, or exemplary embodiments for the corresponding system, are described below:

FIG. 1 illustrates a flowchart-like representation of a preferred exemplary embodiment of the computer-implemented method 100 for determining a refractive power value of an intraocular lens to be inserted. To this end, the method 100 includes measuring, 102, ophthalmological patient data and receiving, 104, a target refraction value. This is the refraction value which the eye is intended to have after the operation—i.e., after the insertion of the intraocular lens. In this case, slight myopia may be intended so that the patient can for example read without glasses following the operation. However, the value of the target refraction value may also be specified as zero.

Further, the method 100 includes determining, 106, by means of a physical or physical-optical model, a first refractive power value of an intraocular lens to be inserted. Formulas known from the prior art are suitable to this end. By way of example, use can be made of empirical formulas, regression forms, lookup tables, or else a second machine learning system (e.g., a support vector machine). In any case, the measured ophthalmological patient data—or a subset of the data—and the target refraction value are used as input data.

Moreover, the method includes determining, 108, by means of a trained machine learning system, a second refractive power value of the intraocular lens to be inserted. The latter was trained in advance using ophthalmological training data—i.e., a set of training vectors —, respectively associated target refraction values and respectively associated refractive power values of an intraocular lens to be inserted. In this case, the respectively associated refractive power values of the intraocular lens to be inserted serve as ground truth data for determining a corresponding machine learning model for the machine learning system. To arrive at the desired result, it is then necessary to use the measured ophthalmological patient data and the received target refraction value as input data for the trained machine learning system. In an exemplary embodiment, it is also possible to use a plurality of physical models or else a plurality of machine learning systems, each with different learning models. The respectively determined boosting factor values were used as additional intermediate results for the final refractive power of the intraocular lens to be inserted.

Finally, the method 100 additionally includes determining, 110, the final refractive power value of the intraocular lens to be inserted from the first refractive power value and the second refractive power value by means of an individual boosting factor value. In this case, the boosting factor is fundamentally indicative of how well a patient vector, whose components are determined by the measured ophthalmological input data, fits to the domain of the training data used to train the machine learning system.

As already mentioned above, an equivalent method or system can be used to determine not the final refractive power of the intraocular lens to be inserted but rather the resultant refraction value (in other words, the target refraction value) using the actually used refractive power of the intraocular lens to be inserted as a starting point.

Optionally, a transportation or robotic system, which takes an intraocular lens to be inserted with the determined refractive power from storage, may be connected to the respective system.

Figure 2:
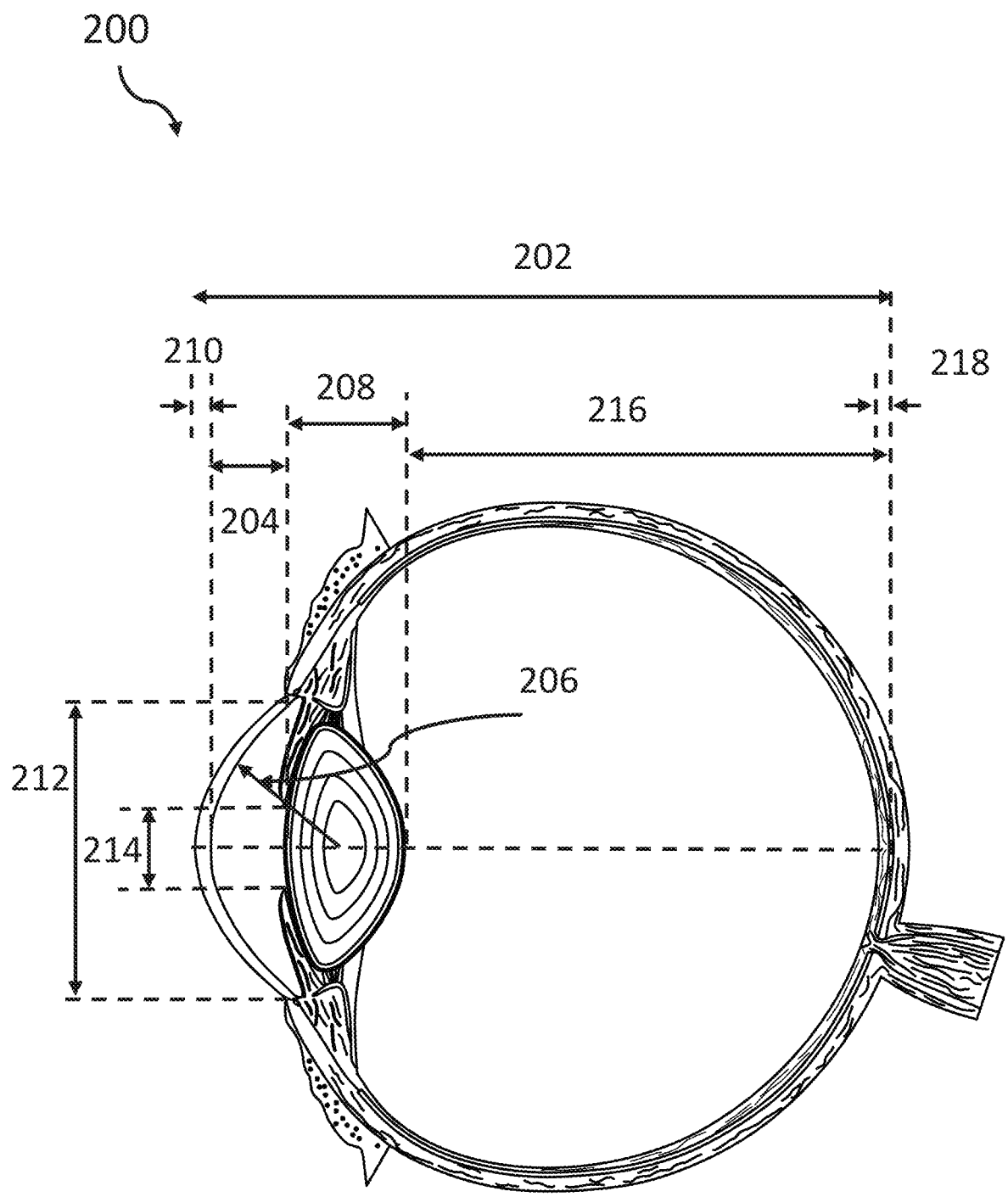
FIG. 2 shows an eye with potential parameter measurement values.

FIG. 2 depicts an eye 200 with different biometric parameters of the eye. In particular, the following parameters are represented: axial length 202 (AL), anterior chamber depth 204 (ACD), keratometry value 206 (K, radius), refractive power of the lens, lens thickness 208 (LT), central cornea thickness 210 (CCT), white-to-white distance 212 (WTW), pupil size 214 (PS), posterior chamber depth 216 (PCD), retina thickness 218 (RT).

Figure 3:
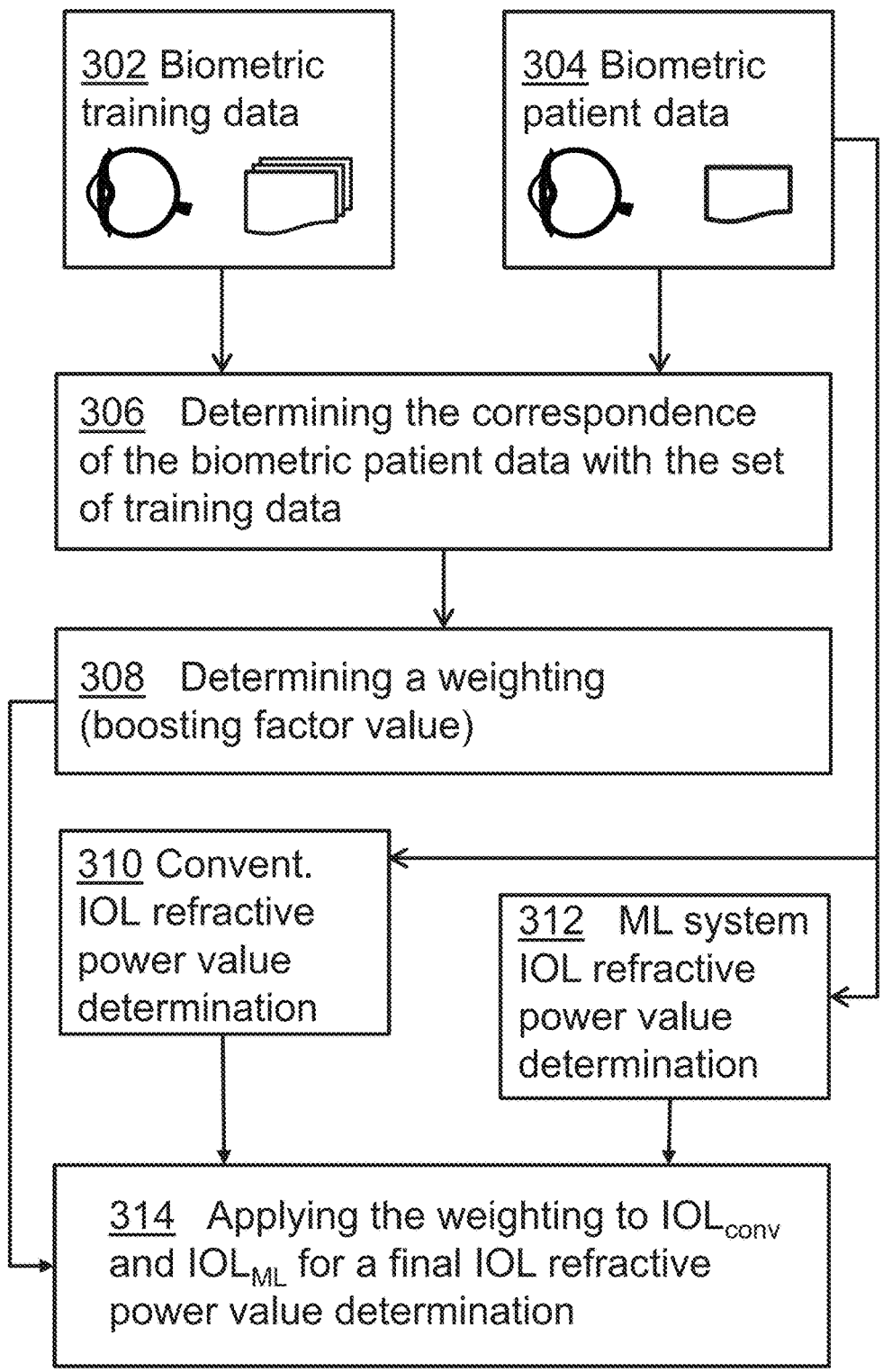
FIG. 3 shows an exemplary embodiment of the method for determining refractive power, which is closer to what is implemented in practice.

FIG. 3 shows an exemplary embodiment 300 of the method for determining refractive power, which is closer to what is implemented in practice. Initially, the set of biometric training data 302 is made available. Secondly, biometric data which are based on ophthalmological patient data 304 are determined—e.g., by a measurement.

Next, the correspondence of the biometric patient data with the set of training data is determined 306, whereupon this is followed by a determination 308 of a weighting (boosting factor value).

The biometric patient data 304 are used directly both in the calculation of the conventional IOL refractive power value determination 310 and in the IOL refractive power value determination 312 by the machine learning system. In a further step of this overview of the method, there then is the application 314 of the weighting (individual boosting factor value) from the conventionally determined IOL refractive power value and the IOL refractive power value determined using the machine learning system, in order, in the end, to carry out the ultimate, final IOL refractive power value determination.

Figure 4:
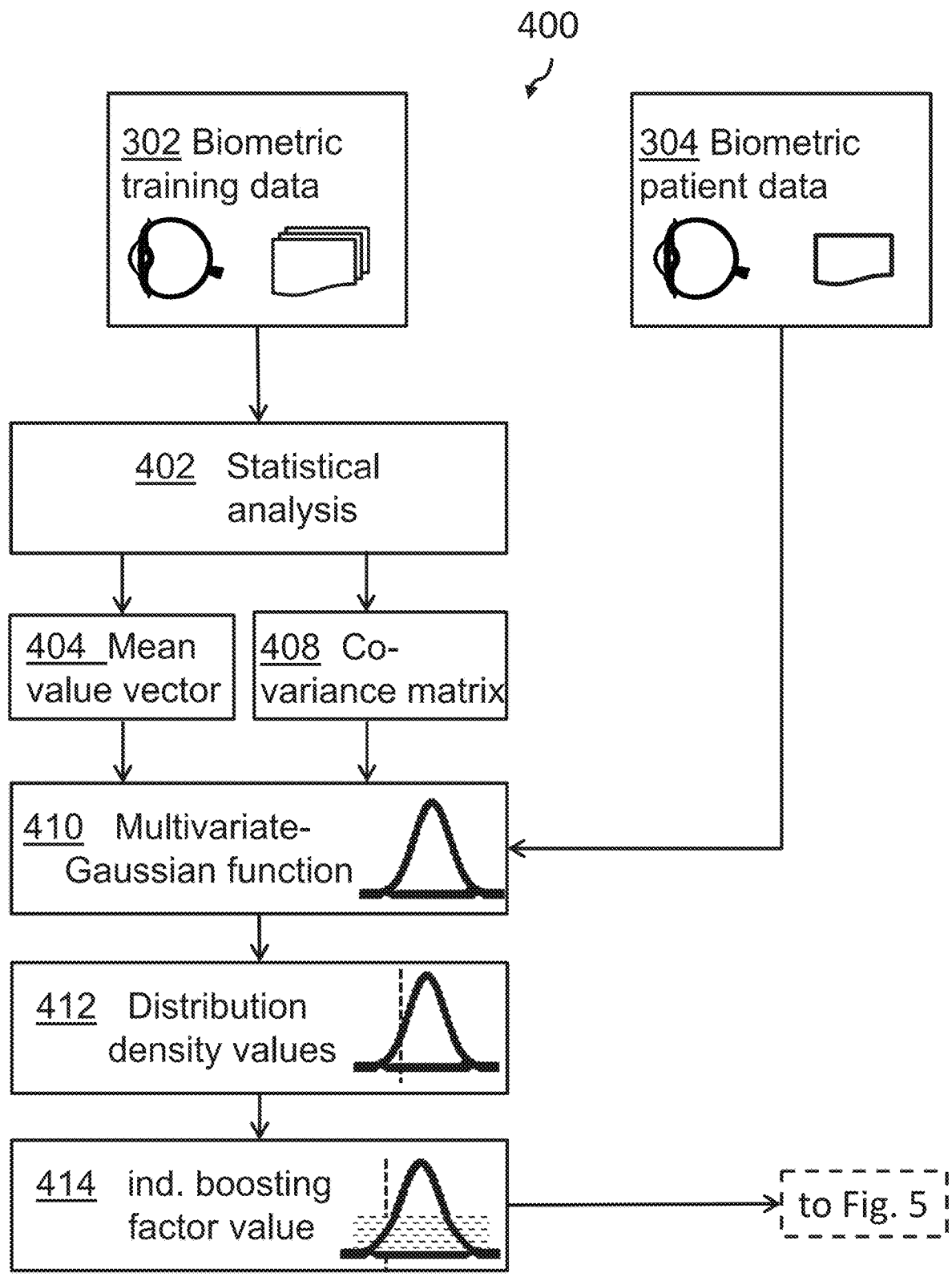
FIG. 4 shows a first part of a flowchart of an exemplary embodiment of the method for determining a refractive power value of an intraocular lens to be inserted.

FIG. 4 shows a first part of a flowchart of an exemplary embodiment 400 of the method for determining a refractive power value of an intraocular lens to be inserted (or else for the determination of the resultant refraction value). This is a representation of the procedure which is relatively close to the implementation. Here, too, the at least partly biometric training data 302 and biometric patient data 304 are starting points for the method.

Initially there is a statistical analysis 402 of the training data. This can be implemented using conventional statistical methods, regression analyses or else a rule-based procedure. The statistical analysis 402 supplies two results, specifically the mean value vector 404 (as already described hereinabove) and the covariance matrix 408. From these two results it is possible to determine the multivariate Gaussian function 410, and this can be used to determine distribution density values 412. It is now possible to determine the individual boosting factor value—in accordance with the formula already specified hereinabove—on the basis thereof. The part of the representation described up until this point, which is relatively close to what is implemented, is therefore characterized by the analysis and the comparison of the measured patient data with the originally used training data for the machine learning system, to be used, for predicting the refractive power (or the resultant refraction value). The description of the method is continued with the next figure.

Figure 5:
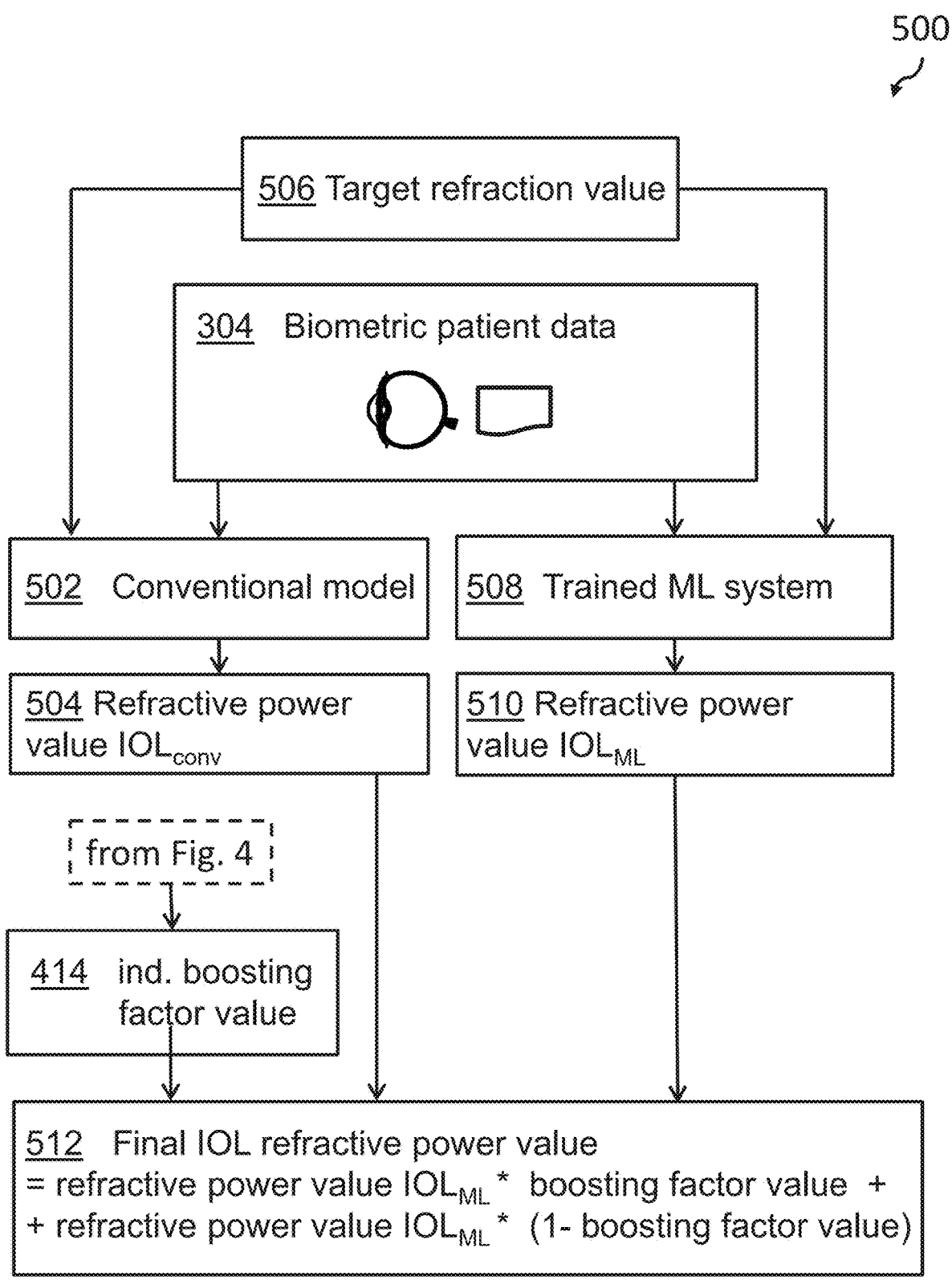
FIG. 5 shows a second part of a flowchart of an exemplary embodiment of the method for determining a refractive power value of an intraocular lens to be inserted.

FIG. 5 shows a second part 500 of a flowchart of an exemplary embodiment of the method for determining a refractive power value of an intraocular lens to be inserted.

This part also starts with the biometric patient data 304. To this end, a target refraction value 506 is made available by way of an input option to the system on which the method is carried out. Here, too, a first refractive power value 504 is determined using a conventional model 502 for determining the refractive power. The second refractive power value 510 can be determined (on the basis of a corresponding learning model) in parallel or subsequently on the basis of the biometric patient data 304 using the trained machine learning system 508.

Then, the final IOL refractive power value 512 is determined according to the specified formula using the individual boosting factor value 414 determined in the first part of the method according to FIG. 4.

For the parallel method according to which a potential target refraction value/resultant refraction value can be determined using a refractive power value as a starting point, the part of the method described in the context of FIG. 4 is identical.

Figure 6:
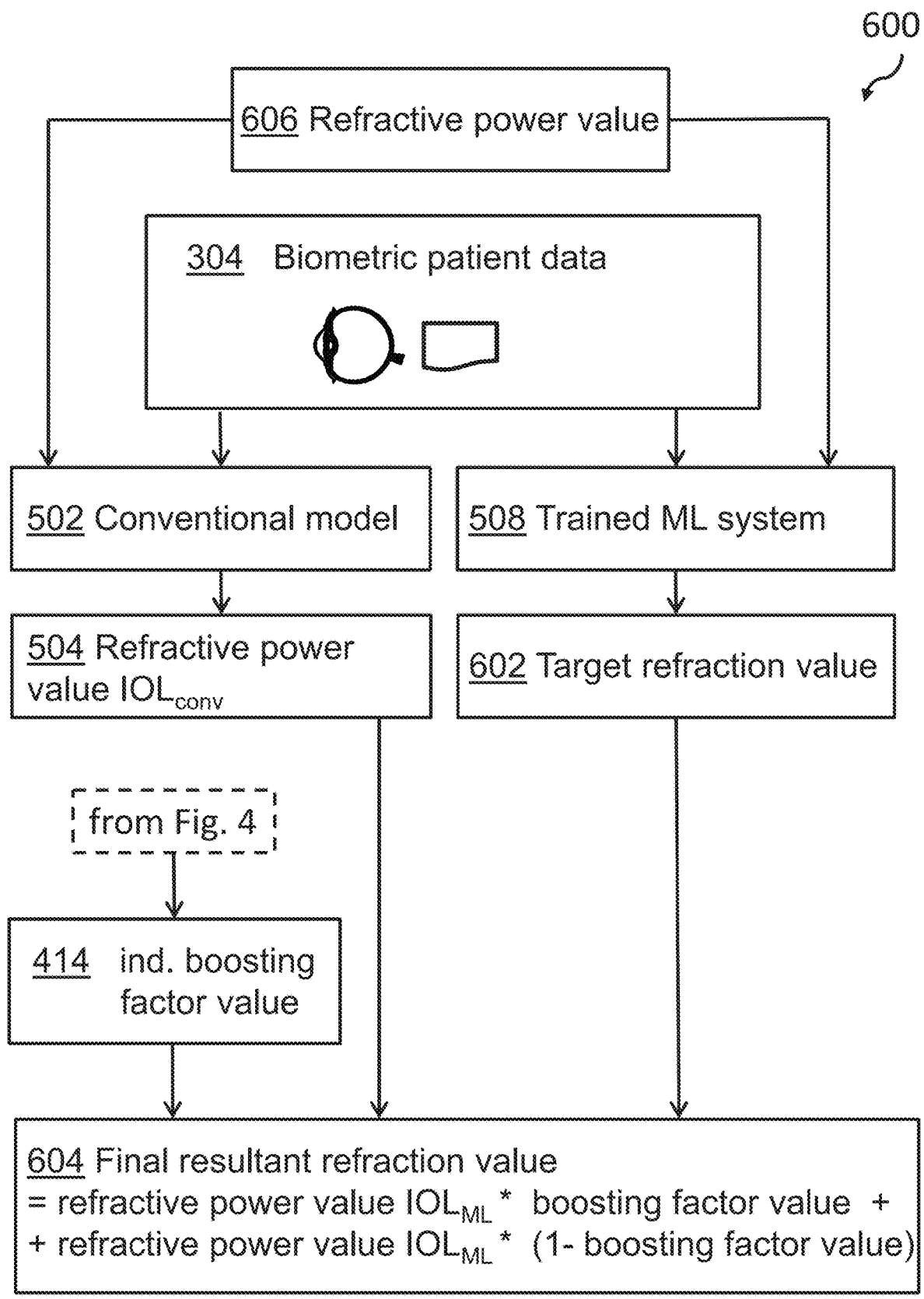
FIG. 6 shows a different second part of a flowchart of an exemplary embodiment of the method for determining a target refraction value—or resultant refraction value—of an intraocular lens to be inserted.

However, FIG. 6 shows a different second part of a flowchart 600 of an exemplary embodiment of the method for determining a target refraction value of the patient's eye with the inserted intraocular lens. To this end, the system is provided with the refractive power value 606 of a physically existing IOL. The correspondingly trained machine learning system 508 could have the same hyperparameter values as the trained machine learning system according to FIG. 5. However, different training data would naturally be used (see above), with the result that a different learning model (i.e., different parameter values) would be generated by the training.

In this case, the trained machine learning system 508 would determine or predict a second target refraction value 602, which is then used together with the conventionally determined first target refraction value 604 and the individual boosting factor value 414 in order to determine the final resultant refraction value 604 in accordance with the formula specified there.

Figure 7:
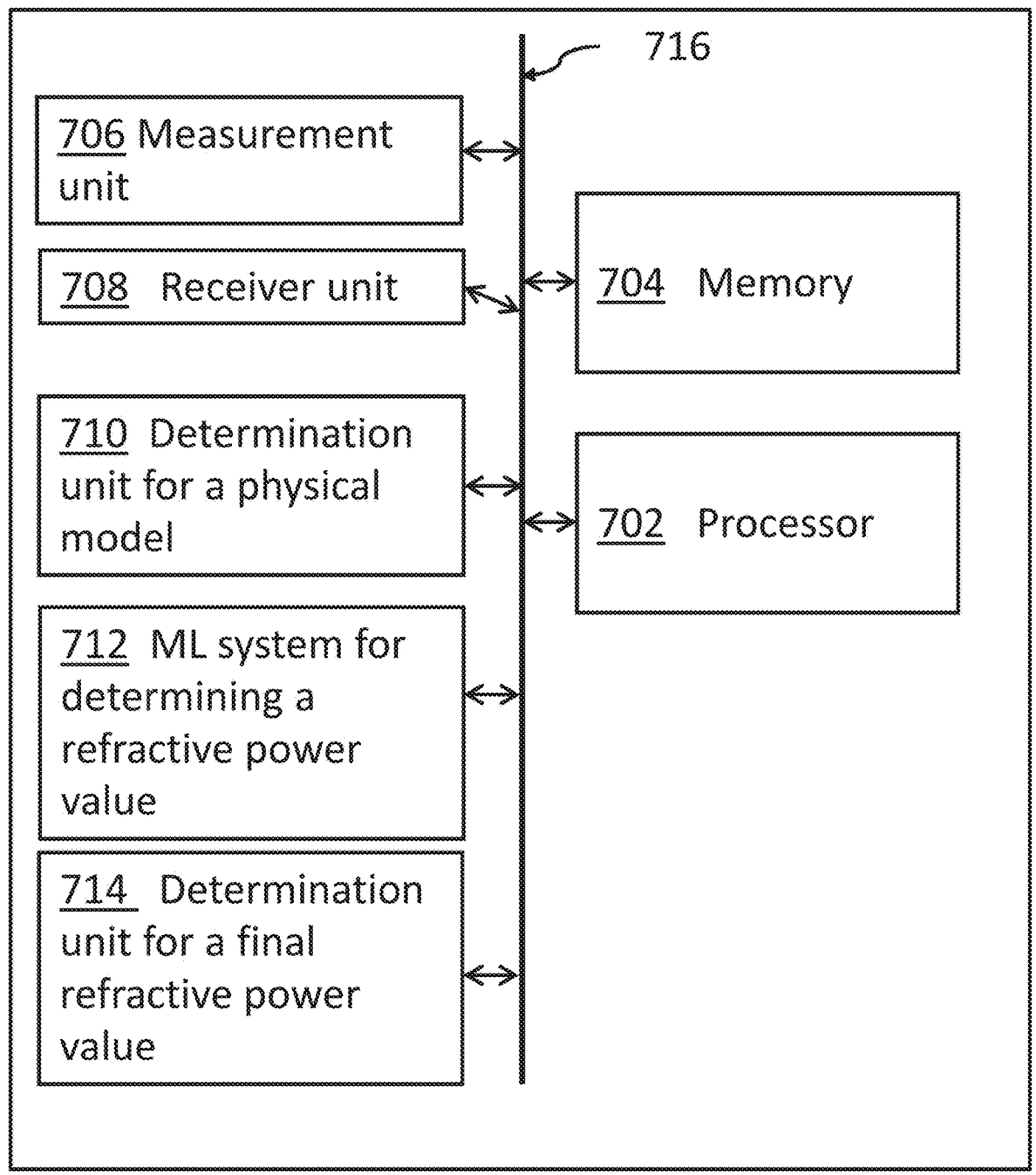
FIG. 7 shows a diagram of a system for determining refractive power.

FIG. 7 shows a diagram of a system 700 for determining a refractive power value of an intraocular lens to be inserted. Attention is drawn to the fact that a very similar or comparable system can be used to determine the post-operative refraction value. The machine learning system would be trained using different training data, as already sketched out above.

To this end, the system 700 for determining a refractive power value of an intraocular lens to be inserted comprises the following: a processor 702 and a memory 704 which operatively cooperates with the processor 702 to store instructions which, when executed by the processor 702, prompt the processor 704 to do the following: to measure—in particular using a measurement unit 706—ophthalmological patient data and to receive—for example by means of a receiver unit 708—a target refraction value. To this end, the target refraction value or the refractive power value can optionally be input. These alternatives have already been described above.

Moreover, the processor is prompted to determine the refractive power value by means of the physical model on the one hand and by means of the trained machine learning system on the other hand; to this end, use can be made for example of a refractive power value determination unit 710 for the physical model and a correspondingly trained machine learning system 712 (either for predicting the refractive power value of the IOL or for predicting the target refraction value using the IOL as a starting point). The final refractive power value determination (or the resultant refraction value) is then determined for the final refractive power value by means of the determination unit 714, with the boosting factor value being used.

Express reference is made to the fact that the modules and units—in particular the processor 702, the memory 704, the measurement unit 706, the receiver unit 708, the determination unit 710 for the physical model, the trained machine learning system 712 for the refractive power value determination (or the resultant refraction value) and the determination unit 714 for the final refractive power value (or the resultant refraction value)—may be connected by electrical signal lines or by way of a system-internal bus system 716 for the purposes of interchanging signals or data.

Figure 8:
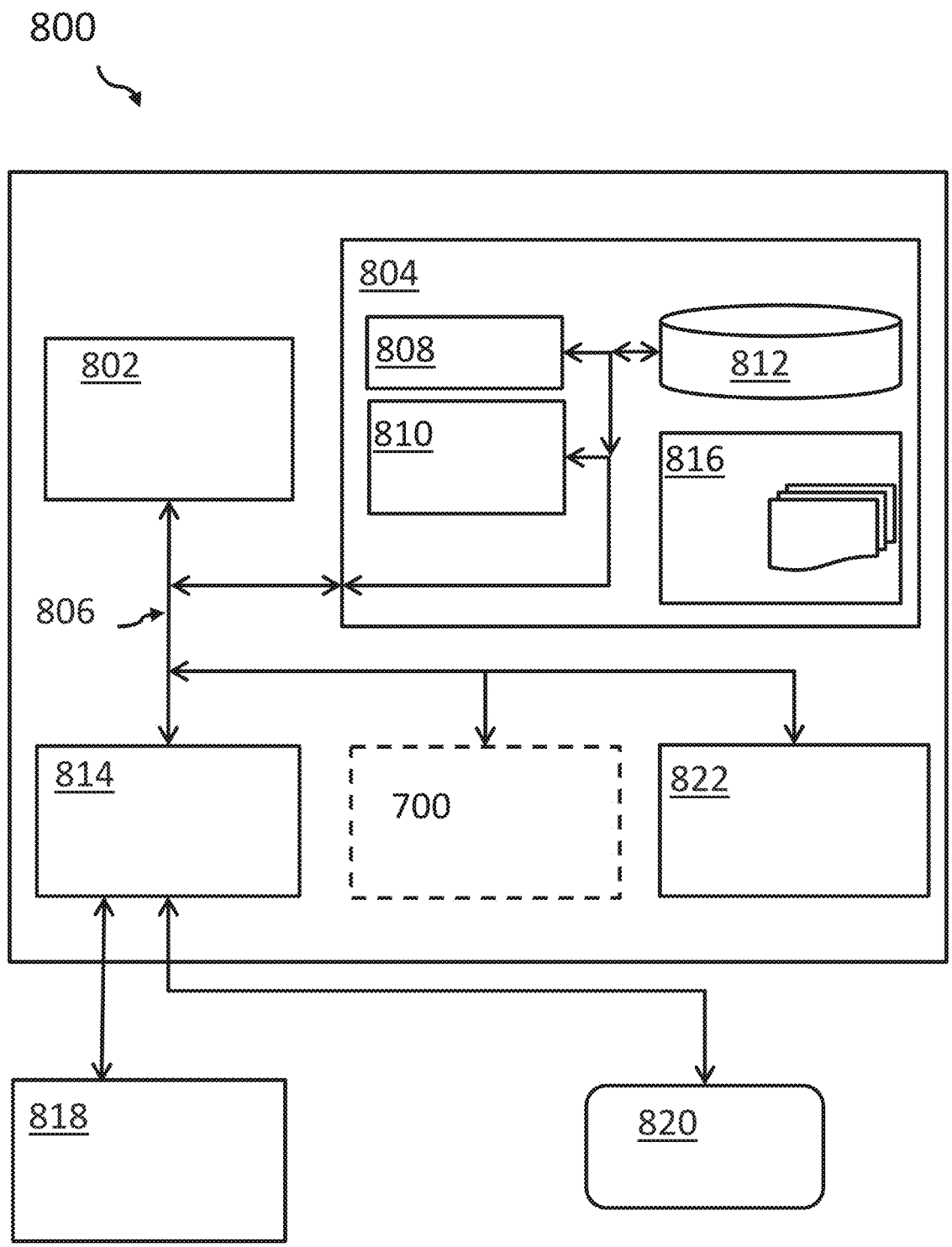
FIG. 8 illustrates an exemplary embodiment of a computer system which comprises the system according to FIG. 7.

FIG. 8 illustrates an exemplary embodiment of a computer system 800 which also comprises the system according to FIG. 7. The computer system 800 has a plurality of general-purpose functions. The computer system may in this case be a tablet computer, a laptop/notebook computer, some other portable or mobile electronic device, a microprocessor system, a microprocessor-based system, a smartphone, a computer system with specially configured special functions, or else a constituent part of a microscope system. The computer system 800 may be configured so as to execute computer system-executable instructions—such as for example program modules—that may be executed in order to implement functions of the concepts proposed here. For this purpose, the program modules can comprise routines, programs, objects, components, logic, data structures etc. in order to implement particular tasks or particular abstract data types.

The components of the computer system may comprise the following: one or more processors or processing units 802, a storage system 804 and a bus system 806 that connects various system components, including the storage system 804, to the processor 802. The computer system 800 typically comprises a plurality of volatile or non-volatile storage media accessible by the computer system 800. The storage system 804 can store the data and/or instructions (commands) of the storage media in volatile form—such as for example in a RAM (random access memory) 808—in order to be executed by the processor 802. These data and instructions realize one or more functions and/or steps of the concept presented here. Further components of the storage system 804 may be a permanent memory (ROM) 810 and a long-term memory 812, in which the program modules and data (reference sign 816) and also workflows may be stored.

The computer system has a number of dedicated devices (keyboard 818, mouse/pointing device [not illustrated], screen 820, etc.) for communication purposes. These dedicated devices can also be combined in a touch-sensitive display. An I/O controller 814, provided separately, ensures a frictionless exchange of data with external devices. A network adapter 822 is available for communication via a local or global network (LAN, WAN, for example via the Internet). The network adapter can be accessed by other components of the computer system 800 via the bus system 806. It is understood in this case, although it is not illustrated, that other devices can also be connected to the computer system 800.

Additionally, at least parts of the system 700 for determining a refractive power value of an intraocular lens to be inserted (cf. FIG. 7) may also be connected to the bus system 806. The system 700 and the computer system 800 may optionally use the memories and/or the processor(s) jointly. This likewise applies analogously to the system for determining the resultant refraction value (also referred to as determining the target refraction value).

The description of the various exemplary embodiments of the present disclosure has been given for the purpose of improved understanding but does not serve to directly restrict the inventive concept to these exemplary embodiments. A person skilled in the art will himself/herself develop further modifications and variations. The terminology used here has been selected so as to best describe the basic principles of the exemplary embodiments and to make them easily accessible to a person skilled in the art.

The principle presented here may be embodied as a system, as a method, combinations thereof and/or else as a computer program product. The computer program product can in this case comprise one (or more) computer-readable storage medium/media comprising computer-readable program instructions in order to cause a processor or a control system to implement various aspects of the present disclosure.

Electronic, magnetic, optical, electromagnetic or infrared media or semiconductor systems are used as forwarding medium; for example SSDs (solid state devices/drives as solid state memory), RAM (random access memory) and/or ROM (read-only memory), EEPROM (electrically erasable ROM) or any combination thereof. Suitable forwarding media also include propagating electromagnetic waves, electromagnetic waves in waveguides or other transmission media (for example light pulses in optical cables) or electrical signals transmitted in wires.

The computer-readable storage medium may be an embodying device that retains or stores instructions for use by an instruction execution device. The computer-readable program instructions that are described here may also be downloaded onto a corresponding computer system, for example as a (smartphone) app from a service provider via a cable-based connection or a mobile radio network.

The computer-readable program instructions for executing operations of the disclosure described here may be machine-dependent or machine-independent instructions, microcode, firmware, status-defining data or any source code or object code that is written for example in C++, Java or the like or in conventional procedural programming languages such as for example the programming language "C" or similar programming languages. The computer-readable program instructions may be executed in full by a computer system. In some exemplary embodiments, there may also be electronic circuits, such as, for example, programmable logic circuits, field-programmable gate arrays (FPGAs) or programmable logic arrays (PLAs), which execute the computer-readable program instructions by using status information of the computer-readable program instructions in order to configure or to individualize the electronic circuits according to aspects of the present disclosure.

The disclosure proposed here is furthermore illustrated with reference to flowcharts and/or block diagrams of methods, apparatuses (systems) and computer program products according to exemplary embodiments of the disclosure. It should be pointed out that practically any block of the flowcharts and/or block diagrams can be embodied as computer-readable program instructions.

The computer-readable program instructions may be made available to a general-purpose computer, a special computer or a data processing system able to be programmed in another way in order to create a machine such that the instructions that are executed by the processor or the computer or other programmable data processing devices generate means for implementing the functions or procedures that are illustrated in the flowchart and/or block diagrams. These computer-readable program instructions can correspondingly also be stored on a computer-readable storage medium.

In this sense, any block in the illustrated flowchart or the block diagrams may represent a module, a segment or portions of instructions that represent a plurality of executable instructions for implementing the specific logic function. In some exemplary embodiments, the functions represented in the individual blocks can be implemented in a different order—optionally also in parallel.

The illustrated structures, materials, sequences, and equivalents of all of the means and/or steps with associated functions in the claims below are intended to apply all of the structures, materials or sequences as expressed by the claims.

What is claimed is:

1. A computer-implemented method for determining a refractive power value of an intraocular lens to be inserted, the method comprising:
   measuring ophthalmological patient data;
   receiving a target refraction value;
   determining, using a physical model, a first refractive power value of the intraocular lens to be inserted, with the measured ophthalmological patient data and the target refraction value being used as input data;

determining, using a trained machine learning system, a
second refractive power value of the intraocular lens to
be inserted,
wherein the machine learning system was trained using
ophthalmological training data, respectively associated target refraction values and respectively associated refractive power values of the intraocular lens
to be inserted, the respectively associated refractive
power values of the intraocular lens to be inserted
serving as ground truth data for determining a corresponding machine learning model for the machine
learning system,
the measured ophthalmological patient data and the
received target refraction value being used as input
data for the trained machine learning system; and
determining a final refractive power value of the intraocular lens to be inserted from the first refractive power
value and the second refractive power value by means
of an individual boosting factor value, the boosting
factor being indicative of how well a patient vector,
whose components are determined by the measured
ophthalmological patient data, fits to a domain of the
ophthalmological training data used to train the
machine learning system.

2. The method of claim 1, wherein the final refractive power value (PowerIOL) of the intraocular lens to be inserted is determined from the first refractive power value and the second refractive power value using the individual boosting factor value (BF) as PowerIOL=$BF$*second refractive power value+(1−$BF$)*first refractive power value.

3. The method of claim 1, wherein a determination of the individual boosting factor value comprises:
applying a statistical analysis method to the ophthalmological training data and, on a basis thereof,
determining an average vector, and
determining a covariance matrix.

4. The method of claim 3, wherein determining the individual boosting factor value comprises using a multivariate Gaussian function which was determined using the ophthalmological training data.

5. The method of claim 4, wherein determining the individual boosting factor value comprises scaling a distribution density value which arises as a result of using the multivariate Gaussian function to an interval of [0, 1].

6. The method of claim 1, additionally comprising transmitting the final refractive power value and/or the individual boosting factor value to at least one output device.

7. A computer-implemented method for determining a target refraction value on a basis of a refractive power of an intraocular lens to be inserted, the method comprising:
measuring ophthalmological patient data;
receiving a refractive power value of the intraocular lens to be inserted;
determining, using a physical model, a first target refraction value, with the measured ophthalmological patient data and the refractive power value of the intraocular lens to be inserted being used as input data;
determining, using a trained machine learning system, a second target refraction value,
wherein the machine learning system was trained using ophthalmological training data, respective associated refractive power values of the intraocular lens to be inserted and respective associated target refraction values, the respective associated target refraction values serving as ground truth data for determining a corresponding machine learning model for the machine learning system,
the measured ophthalmological patient data and the received refractive power value being used as input data for the trained machine learning system; and
determining a final target refraction value from the first target refraction value and the second target refraction value by means of an individual boosting factor value, the boosting factor being indicative of how well a patient vector, whose components are determined by the measured ophthalmological patient data, fits to a domain of the ophthalmological training data used to train the machine learning system.

8. A computer program product for determining a target refraction value on a basis of a refractive power of an intraocular lens to be inserted, wherein the computer program product comprises a computer-readable storage medium having program instructions stored thereon, the program instructions being executable by one or more processors and prompting the one or more processors to carry out the method of claim 7.

9. A system for determining a refractive power value of an intraocular lens to be inserted, the system comprising:
a processor; and
a memory operatively coupled to the processor and storing instructions that, when executed by the processor, enable the processor to:
measure ophthalmological patient data;
receive a target refraction value;
determine, using a physical model, a first refractive power value of the intraocular lens to be inserted, with the measured ophthalmological patient data and the target refraction value being used as input data;
determine, using a trained machine learning system, a second refractive power value of the intraocular lens to be inserted,
wherein the machine learning system was trained using ophthalmological training data, respectively associated target refraction values and respectively associated refractive power values of the intraocular lens to be inserted, the respectively associated refractive power values of the intraocular lens to be inserted serving as ground truth data for determining a corresponding machine learning model for the machine learning system,
the measured ophthalmological patient data and the received target refraction value being used as input data for the trained machine learning system; and
determine a final refractive power value of the intraocular lens to be inserted from the first refractive power value and the second refractive power value by means of an individual boosting factor value, the boosting factor being indicative of how well a patient vector, whose components are determined by the measured ophthalmological patient data, fits to a domain of the ophthalmological patient data used to train the machine learning system.

10. A system for determining a target refraction value on a basis of a refractive power of an intraocular lens to be inserted, the system comprising:
a processor; and
a memory operatively coupled to a processor and storing instructions that, when executed by the processor, enable the processor to perform a method to determine the target refraction value on the basis of the refractive power of the intraocular lens to be inserted, the method comprising:

measuring ophthalmological patient data;

receiving a refractive power value of the intraocular lens to be inserted;

determining, using a physical model, a first target refraction value, with the measured ophthalmological patient data and the refractive power value of the intraocular lens to be inserted being used as input data;

determining, using a trained machine learning system, a second target refraction value, wherein the machine learning system was trained using ophthalmological training data, respective associated refractive power values of the intraocular lens to be inserted and respective associated target refraction values, the respective associated target refraction values serving as ground truth data for determining a corresponding machine learning model for the machine learning system, the measured ophthalmological patient data and the received refractive power value being used as input data for the trained machine learning system; and determining a final target refraction value from the first target refraction value and the second target refraction value by means of an individual boosting factor value, the boosting factor being indicative of how well a patient vector, whose components are determined by the measured ophthalmological patient data, fits to a domain of the ophthalmological training data used to train the machine learning system.

11. A computer program product for determining a refractive power value of an intraocular lens to be inserted, wherein the computer program product comprises a computer-readable storage medium having program instructions stored thereon, the program instructions being executable by one or more processors and prompting the one or more processors to carry out the method of claim 1.

* * * * *